United States Patent [19]

Stollar et al.

[11] Patent Number: 4,925,642

[45] Date of Patent: May 15, 1990

[54] PROCESS FOR THE PREPARATION AND THE ISOLATION OF AROMATIC NITRILES

[75] Inventors: Hayman Stollar, Beer-Sheva, Israel; Abram Becker, Paris, France

[73] Assignee: Bromine Compounds Limited, Israel

[21] Appl. No.: 198,155

[22] Filed: May 24, 1988

[30] Foreign Application Priority Data

May 29, 1987 [IL] Israel ............................ 82694

[51] Int. Cl.$^5$ ............................ C07C 253/14
[52] U.S. Cl. .................... 423/364; 558/343; 423/371
[58] Field of Search ............ 558/343; 423/42, 364, 423/371

[56] References Cited

U.S. PATENT DOCUMENTS

| | | | |
|---|---|---|---|
| 1,672,253 | 6/1928 | Giles | 558/343 |
| 2,591,415 | 4/1952 | Engelhardt | 558/343 |
| 3,259,646 | 7/1966 | Harris et al. | 558/343 |

OTHER PUBLICATIONS

Ellis et al, *Chem Rev.*, "Cyanation of Aromatic Halides", vol. 87, pp. 779–794, 1987.

*Primary Examiner*—Joseph Paul Brust
*Assistant Examiner*—Zinna Northington-Davis
*Attorney, Agent, or Firm*—Lerner, David, Littenberg, Krumholz & Mentlik

[57] ABSTRACT

A process is provided by means of which aromatic nitriles can be isolated in high yield. The process comprises reacting an aromatic halogenated compound with cuprous cyanide in a suitable solvent.

The process is suitable for preparing many important materials, such as p-hydroxybenzonitrile.

27 Claims, No Drawings

PROCESS FOR THE PREPARATION AND THE ISOLATION OF AROMATIC NITRILES

FIELD OF THE INVENTION

The present invention relates to a process for the preparation and the isolation of aromatic nitriles, wherein the aromatic nitrile is obtained by reacting aromatic halogenated compounds with cuprous cyanide (CuCN). More particularly the invention relates to processes by means of which the aromatic nitrile can be isolated and, at the same time, the reagent CuCn can be recovered from the reaction mixture.

Also encompassed within the present invention are processes by which the reagent CuCN can be recovered from the reaction mixture resulting from processes for the preparation of aromatic nitriles, which employ such reagent.

BACKGROUND OF THE INVENTION

The reaction employing CuCN is well known in the art and is sometimes called the Rosenmund-von Braun Reaction. The reaction can schematically be represented by:

$$ArX + CuCN \rightarrow ArCN + CuX$$

wherein X represents a halogen atom and the reaction is carried out at a temperature of about 150°–250° C. The reaction is carried out in a variety of solvents, the most commonly employed solvents being polar aprotic solvents such as dimethylformamide, dimethylacetamide and N-methylpyrrolidone. Commonly, an excess of CuCN is employed.

An example of such a process is the preparation of p-hydroxybenzonitrile (HBN) from p-halogenated phenol, which can conveniently be carried out in dimethylacetamide (DMA) as the solvent.

When the reaction is complete the solvent is normally distilled off and the nitrile product is obtained as a complex bound to the cuprous halide which is formed in the reaction. In order to isolate the nitrile product, the complex must be decomposed. Several methods are known in the art to effect this decomposition. In one such method [U.S. Pat. No. 3,259,646] concentrated hydrochloric acid and ferric chloride are added and the product is isolated by extraction into an organic solvent. According to another method [L. Freidman and H. Schechter, J. Org. Chem., Vol. 26, pp. 2522–24 (1961)], ethylene diamine is added and the product is again isolated by solvent extraction. According to a further known method, the cuprous halide is dissolved in an aqeous solution containing 4 molar equivalents of NaCN and the product is extracted with an organic solvent.

The aforementioned and other known isolation methods present several serious drawbacks. The copper halide formed in the reaction is transformed into difficulty recoverable forms, which cannot be recycled as such. Furthermore, in the first mentioned method the formation of highly toxic hydrogen cyanide and cyanogen takes place. In the last two methods a considerable drawback is the alkaline nature of the solutions obtained, which prevents extraction of acidic nitriles into organic solvents.

SUMMARY OF THE INVENTION

It has now been most surprisingly found, and this is an object of the invention, that it is possible to provide a process for obtaining aromatic nitriles, which is free from the abovementioned disadvantages, and which permits to prepare aromatic nitriles in high yields.

It has also been surprisingly found, and this is another object of the invention, that it is possible to provide a process by which the expensive CuCN reagent can be recovered in high yield and acceptable quality, in contrast to existing processes in which this reagent is essentially lost.

It is an object of the invention to provide a process by which the aromatic nitrile can be easily isolated, which process does not present the aforesaid drawbacks.

It is another object of the present invention to provide a process by which the reagent CuCN can be recovered in high yield from the cuprous halide formed in the reaction, in a quality sufficient to permit its recycle, thereby resulting in a considerable economic advantage.

It is a further object of the invention to provide an improved process by which nitriles, such as HBN, can be obtained in very high yields.

DETAILED DESCRIPTION OF THE INVENTION

The process for the preparation and the isolation of aromatic nitriles according to the invention, in which an aromatic halogenated compound is reacted with cuprous cyanide in a suitable solvent, is characterized by the steps of:

(a) adding water to the reaction mixture obtained after the reaction of the aromatic halogenated compound with cuprous cyanide has been substantially completed;

(b) adding an alkali metal cyanide to the resulting mixture;

(c) separating the resulting CuCN suspension; and (d) separating the organic phase to recover the aromatic nitrile;

the amount of alkali metal cyanide added being substantially stoichiometric with the aromatic reagent employed in the reaction.

The alkali metal cyanide added in step (b) can be added together with the water added in step (a), as a solution of the alkali metal cyanide in water, or it can be added in solid form or as a solution or a suspension in an aqueous or non-aqueous solvent medium. Separation of the CuCN suspension can be carried out according to any of the methods known to the man skilled in the art, e.g., by decantation, or by filtration operations, such as centrifugation.

According to a preferred embodiment of the invention, the addition of water is preceded by the step of concentrating the reaction mixture, after completion of the reaction of the aromatic halogenated compound with cuprous cyanide, by removing part of the solvent. Concentrating the solution permits to employ smaller amounts of water in the above step (a), and further provides a convenient way to recover the reaction solvent. As will be apparent to the skilled technician, it is desirable to remove as much solvent as possible in this concentration step. However, care should be taken to avoid temperatures which exceed those permissible for the product involved.

According to a preferred embodiment of the invention, the amount of solvent removed is at least 60% of the total solvent present in the reaction mixture. Removal of 70% to 90% of the total volume of solvent employed has been found to be convenient in most cases.

As will be apparent to the men of the art, the temperature of the mixture may require adjustment before water is added to it. When operating at atmospheric pressure, as customary, this temperature will usually be in the range 30°–110° C., preferably 90° C. to 100° C.

According to a preferred embodiment of the invention, the aromatic halogenated compound is a brominated or chlorinated aromatic compound. According to another preferred embodiment of the invention, the alkali metal is sodium or potassium.

Preferably, the reaction mixture is concentrated by removing the solvent by evaporation, more preferably under vacuum. Especially useful solvents for carrying out the invention are dimethylformamide, dimethylacetamide and N-methyl-pyrrolidone, but any other solvent which can be suitably employed to carry out the reaction can likewise be used.

Whenever the nitrile product is a solid, an organic solvent can be added to dissolve the nitrile product and to permit the separation of the CuCN suspension obtained according to the method of the invention. Any suitable solvent can be employed, as long as it dissolves the nitrile product and does not dissolve the CuCN. Either water miscible solvents such as acetone, tetrahydrofuran or methanol, or water immiscible solvents can be used, as will be apparent to a person skilled in the art.

The invention provides, apart from a preparation process by means of which the aromatic nitrile can be conveniently isolated as hereinbefore stated, also a process for the recovery of CuCN from reaction mixtures containing aromatic nitriles and CuX, wherein X is a halogen atom, which is characterized by the steps of:
(a) adding water to the reaction mixture obtained after the reaction of the aromatic halogenated compound with cuprous cyanide has been substantially completed;
(b) adding an alkali metal cyanide to the resulting mixture; and
(c) separating the resulting CuCN suspension to recover the insoluble CuCN;
the amount of alkali metal cyanide added being substantially stoichiometric with the aromatic reagent employed in the reaction.

The same considerations given above in connection to the process for the preparation and the isolation of aromatic nitriles, with respect to steps (a) to (c) as well as with respect to the addition of water and the concentration of the reaction mixture, apply identically to the process for the recovery of CuCN.

According to a preferred embodiment of the invention the halogen is bromine or chlorine, and the alkali metal is sodium or potassium.

In a preferred embodiment of the invention, the amount of solvent removed is at least 60% of the total solvent present in the reaction mixture. The solvent is preferably removed by evaporation, more preferably under vacuum.

It has further been surprisingly found that the process of the invention can be conveniently exploited for the preparation of HBN. This is surprising because of the acidic nature of this compound, which would have been expected to interfere with the transformation of CuX to CuCN, since under acidic conditions $CN^-$ is essentially entirely in the form of volatile HCN.

p-Hydroxybenzonitrile, whenever obtained by the process of the invention, also forms part of the present invention.

The above and other characteristics and advantages of the invention will be better understood through the following examples, provided for the purpose of illustration.

EXAMPLE 1

Preparation of p-Hydroxybenzonitrile (HBN)

To a one liter 3-necked flask, equipped with a mechanical stirrer, a nitrogen inlet tube, a thermometer and a reflux condenser there were added 350 ml of dimethylacetamide, 116.5 g CuCN (1.3 moles) and 173 g p-bromophenol (1 mole). The reaction was carried out in a nitrogen atmosphere. The contents of the flask were heated to 180° C. and this temperature was maintained by external heating for 3 hours. After this period the flask was equipped for vacuum distillation and 290 ml of DMA were distilled at a pressure of about 3 mm Hg.

After cooling the contents of the flask to 100° C., a solution of 49 g of sodium cyanide (1 mole) in 265 ml of water was added dropwise to the flask during about 15 minutes. The brown suspension that was formed was stirred at 100° C. for one hour and then cooled and filtered. The organic phase from the filtrate was separated. The filter cake was washed with two 100 ml portions of methanol, the combined methanol wash solutions were evaporated and the oily residue was combined with the organic phase from the filtrate. 179 g of a brown oil were obtained, containing 62% of HBN which corresponds to 93% of the theoretical yield. The product was isolated as a white crystalline solid by vacuum distillation in 90% yield and 98.5% purity (by HPLC analysis).

The dried filter cake (113.6 g) contained 67.4% Cu, corresponding to a recovery of 92.8% of the CuCN.

EXAMPLE 2

Preparation of p-Hydroxybenzonitrile (HBN)

To a one liter 3-necked flask equipped with a mechanical stirrer, a dropping funnel, a nitrogen inlet tube, a thermometer and a reflux condenser there were added 270 ml of DMA and 116.5 g of CuCN (1.3 mole). the contents of the flask were heated to reflux under a nitrogen atmosphere, and a solution of 173 g of p-bromophenol (1 mole) in 80 ml of DMA was added dropwise during 1.5 hours allowing the temperature to rise to 170° C. This temperature was maintained for an additional 3 hours, the flask was then equipped for vacuum distillation and 261 ml of DMA were distilled off.

After cooling the contents of the flask to 100° C., a solution of 49 g of sodium cyanide (1 mole) in 265 ml of water was added dropwise to the flask during about 15 minutes. The brown suspension that was formed was stirred at 100° C. for one hour and then cooled and filtered. The organic phase from the filtrate was separated. The filter cake was washed with two 100 ml portions of methanol, the combined methanol wash solutions were evaporated and the oily residue was combined with the organic phase from the filtrate. 192 g of a brown oil were obtained, containing 57.8% of HBN which corresponds to 93% of the theoretical yield.

The dried filter cake (112 g) contained 68.3% Cu, corresponding to a recovery of 92.7% of the CuCN.

EXAMPLE 3

Preparation of HBN with recovered CuCN.

The procedure of Example 2 was repeated using 111 g of the CuCN recovered in the example, and 10 g of fresh CuCN. 191 g of a crude product were obtained, containing 58.3% of HBN corresponding to a 93.6% yield of HBN, together with 121.3 g of recovered wet filter cake.

EXAMPLE 4

Preparation of 4-methoxybenzonitrile.

Operating as in Example 2, a solution of 92.5 g of 4-bromoanisole (0.5 mole) in 40 ml DMA was added dropwise to a refluxing mixture of 58.2 g of CuCN (0.65 mole) and 135 ml of DMA during one hour, while allowing the temperature to rise to 170° C. This temperature was maintained for 6 hours after which time 154 ml of dimethylacetamide were distilled off under vacuum. The contents of the flask were cooled to 100° C. and a solution of 24.5 g NaCN (0.5 mole) in 130 ml of water was added dropwise during 20 minutes. The suspension was stirred at 100° C. for 1.5 hours, cooled to 30° C. and filtered. The filter cake was washed with methanol (4 portions of 100 ml each) followed by 250 ml of dichloroethane.

Evaporation of the dichloroethane solution gave 49.9 g of 4-methoxybenzonitrile (75% yield), m.p. 57°–58° C., 99.9% pure by gas chromatography. The dried filter cake (55 g) contained 70.0% Cu and 28.7% CN, corresponding to a recovery o 93.3% of the CuCN with a purity of about 98.7%.

EXAMPLE 5

Preparation of 4-hydroxybenzonitrile.

Operating according to the procedure of Example 1, a mixture of 200 ml of N-methyl-2-pyrrolidone, 64.4 g of p-chlorophenol (0.5 mole) and 58.2 g (0.65 mole) of CuCN were heated to reflux during 8 hours after which 140 ml of the N-methyl-2-pyrrolidone were distilled off under vacuum. The contents of the flask were cooled to 100° C. and a solution of 24.5 g (0.5 mole) of sodium cyanide in 130 ml of water was added dropwise during 30 minutes. The suspension was stirred at 100° C. for 1 hour, cooled to 30° C. and filtered. The organic phase from the filtrate (78.1 g) was separated and contained 45.7% of HBN according to HPLC assay. The filter cake was washed with three 100 ml portions of methanol and the combined methanol solutions were evaporated, giving 42.5 g of a brown oil containing 41.5% of HBN. The quantity of the HBN in the separated organic phase and in the brown oil from the methanol solutions corresponded to 89.6% of the theoretical yield. The dried filter cake (44.8 g) contained 67.6% Cu and 28.3% CN, corresponding to a recovery of 74.3% of the CuCN with a purity of 96.5%.

EXAMPLE 6

Recovery of CuCN using potassium cyanide.

To a 250 ml flask equipped as in Example 1 there were added 87.5 ml of dimethylacetamide, 29.1 g CuCN (0.325 moles) and 43.3 g (0.25 moles) of p-bromophenol. The contents of the flask were heated to 170° C. and kept at this temperature during 4.5 hours, after which 65 ml of DMA were distilled off under a pressure of 3 mmHg. The reaction mixture was cooled to 105° C. and a solution of 16.3 g (0.25 moles) of potassium cyanide in 65 ml of water was added dropwise to the flask during 0.5 hour. The resulting suspension was stirred at 100° C. during one hour and then cooled and filtered. The organic phase from the filtrate was separated. The filter cake was washed with three 50 ml portions of methanol, the combined methanol wash solutions were evaporated and the oily residue was combined with the organic phase from the filtrate. 48 g of a brown oil were obtained, containing 57.3% of HBN which corresponds to 92.5% of the theoretical yield. The dried filter cake contained 97% of the theoretical yield of CuCN in which the molar ratio of Cu to CN was 1.00.

EXAMPLE 7

Preparation of HBN without distillation of the solvent.

To a reaction mixture prepared according to Example 2, before the distillation step, and having a temperature of 100° C., there was added a solution of 49 g of sodium cyanide (1 mole) in 265 ml of water, followed by an additional 260 ml of water. The suspension was stirred at 100° C. for one hour and then cooled and filtered. The filtrate was saturated with 75 g of sodium chloride and the organic phase was separated. The filter cake was washed with two 100 ml portions of methanol, the combined methanol wash solutions were evaporated and the oily residue was combined with the organic phase from the filtrate. 240 g of brown oil were obtained containing 35.2% of HBN which corresponds to 71% of the theoretical yield. In addition, 120 g of wet filter cake were obtained containing 54.3% Cu, corresponding to a recovery of 78.9% of the CuCN.

EXAMPLE 8

Isolation of HBN with addition of solid NaCN.

To a reaction mixture prepared according to Example 1, after distilling off 300 ml of DMA and maintaining the temperature at 100° C., there were added 265 ml of water. A stirrable paste was formed to which there were added in portions 49 g of solid sodium cyanide (1 mole), and the brown suspension that formed was stirred at 85° C. for one hour and then cooled and filtered. The yield of HBN was 94% of the theoretical yield. In addition 117.6 gr of dried filter cake were obtained containing 68.3% copper, which corresponds to a recovery of 97.2% of the cuprous cyanide.

The above examples have been given for the purpose of illustration and are not intended to be limitative. Many variations can be effected in the processes of the invention. For instance, different organic solvents can be employed and different aromatic nitriles prepared, all without exceeding the scope of the invention.

What we claim is:

1. A method for the isolation of aromatic nitriles from a reaction mixture provided by the Rosenmund-von Braun reaction of a ring halogenated aromatic compound with cuprous cyanide in an organic solvent in which said aromatic nitrile is soluble and said cuprous cyanide is insoluble, said method comprising:
   (a) adding water to said reaction mixture after said reaction is substantially completed so that said reaction mixture includes an aqueous phase and an organic phase comprising said aromatic nitrile and said organic solvent;

(b) adding an alkaline metal cyanide to said reaction mixture, in a quantity substantially stoichiometric with said ring halogenated aromatic compound, thereby forming a suspension of said cuprous cyanide;

(c) separating said suspension of said cuprous cyanide; and (d) separating said organic phase comprising said aromatic nitrile and said organic solvent.

2. The method of claim 1, further comprising the step of recovering said aromatic nitrile from said organic phase.

3. The method of claim 1, further comprising the step of removing a portion of said organic solvent from said reaction mixture prior to said addition of water to said mixture.

4. The method of claim 3, wherein at least 60% of said organic solvent present in said reaction mixture is removed prior to said addition of water.

5. The method of claim 3, wherein said organic solvent is removed by evaporation.

6. The method of claim 1, further comprising the step of dissolving said alkali metal cyanide in said water prior to the addition of said alkali metal cyanide and said water to said reaction mixture.

7. The method of claim 1, wherein said alkali metal cyanide is added as a solution or a suspension in an aqueous or non-aqueous solvent.

8. The method of claim 1, wherein said alkali metal cyanide is added to said reaction mixture in solid form.

9. The method of claim 1, further comprising the step of adjusting the temperature of said reaction mixture to a temperature within the range of between about 30° C. and about 110° C. prior to the addition of said water.

10. The method of claim 1, wherein said ring halogenated aromatic compound is selected from the group consisting of ring brominated aromatic compounds and ring chlorinated aromatic compounds.

11. The method of claim 1, wherein said alkali metal is selected from the group consisting of sodium and potassium.

12. The method of claim 1, wherein said organic solvent is selected from the group consisting of dimethylformamide, dimethylacetamide and N-methylpyrrolidone.

13. The method of claim 12, wherein said aromatic nitrile is p-hydroxybenzonitrile.

14. The method of claim 1, further comprising the step of adding to said reaction mixture an organic solvent to obtain a reaction mixture in which said aromatic nitrile is soluble, prior to separating said cuprous cyanide suspension.

15. The method of claim 1, wherein said reaction mixture further comprises a copper halide.

16. A method for the isolation of aromatic nitriles from a reaction mixture provided by the Rosemund-von Braun reaction of a ring brominated or ring chlorinated aromatic compound with cuprous cyanide in an organic solvent in which said aromatic nitrile is soluble and said cuprous cyanide is insoluble, said method comprising:

(a) adding water to said reaction mixture after said reaction is substantially completed so that said reaction mixture includes an aqueous phase and an organic phase comprising said aromatic nitrile and said organic solvent;

(b) adding an alkali metal cyanide to said reaction mixture in a quantity substantially stoichiometric with said ring brominated or ring chlorinated aromatic compound, thereby forming a suspension of said cuprous cyanide;

(c) separating said suspension of said cuprous cyanide; and (d) separating said organic phase comprising said aromatic nitrile and said organic solvent.

17. A method for the isolation of CuCN from a reaction mixture comprising aromatic nitriles and copper halides provided by Rosemund-von Braun reaction of a ring halogenated aromatic compound with CuCN in an organic solvent in which said aromatic nitrile is soluble and said CuCN is insoluble, said method comprising;

(a) adding water to said reaction mixture after said reaction is substantially completed;

(b) adding an alkali metal cyanide to said reaction mixture, in a quantity substantially stoichiometric with said ring halogenated aromatic compound, thereby forming a suspension of said CuCN; and (c) separating said suspension of said CuCN from said reaction mixture, thereby recovering said CuCN.

18. The method of claim 17, further comprising the step of removing a portion of said organic solvent from said reaction mixture prior to said addition of water to said mixture.

19. The method of claim 18, wherein at least 60% of said organic solvent present in said reaction mixture is removed prior to said addition of water.

20. The method of claim 18, wherein said organic solvent is removed by evaporation.

21. The method of claim 17, further comprising the step of dissolving said alkali metal cyanide in said water prior to the addition of said alkali metal cyanide and said water to said reaction mixture.

22. The method of claim 17, wherein said alkali metal cyanide is added as a solution or a suspension in an aqueous or non-aqueous solvent.

23. The method of claim 17, wherein said alkali metal cyanide is added to said reaction mixture in solid form.

24. The method of claim 17, further comprising the step of adjusting the temperature of said reaction mixture to a temperature within the range of between about 30° C. and about 110° C. prior to said addition of said water.

25. The method of claim 17, wherein said ring halogenated aromatic compound is selected from the group consisting of ring brominated aromatic compounds and ring chlorinated aromatic compounds.

26. The method of claim 17, wherein said alkali metal is selected from the group consisting of sodium and potassium.

27. A method for the isolation of CuCN from a reaction mixture comprising aromatic nitriles and copper halides provided by the Rosemund-von Braun reaction of a ring brominated or ring chlorinated aromatic compound with CuCN in an organic solvent in which said aromatic nitrile is soluble and said CuCN is insoluble, said method comprising:

(a) adding water to said reaction mixture after said reaction is substantially completed;

(b) adding an alkali metal cyanide to said reaction mixture, in a quantity substantially stoichiometric with said ring brominated or ring chlorinated aromatic compound, thereby forming a suspension of said CuCN; and (c) separating said suspension of said CuCN from said reaction mixture, thereby recovering said CuCN.

* * * * *